(12) United States Patent
Terunuma et al.

(10) Patent No.: US 8,611,496 B2
(45) Date of Patent: Dec. 17, 2013

(54) RADIATION TREATMENT SYSTEM

(75) Inventors: Toshiyuki Terunuma, Ibaraki (JP); Takeji Sakae, Ibaraki (JP); Masaru Sato, Ibaraki (JP); Masaya Ishida, Ibaraki (JP)

(73) Assignee: University of Tsukuba, Tsukuba-shi (JP)

( * ) Notice: Subject to any disclaimer, the term of this patent is extended or adjusted under 35 U.S.C. 154(b) by 155 days.

(21) Appl. No.: 13/127,784

(22) PCT Filed: Nov. 12, 2009

(86) PCT No.: PCT/JP2009/069271
§ 371 (c)(1),
(2), (4) Date: Jun. 21, 2011

(87) PCT Pub. No.: WO2010/055881
PCT Pub. Date: May 20, 2010

(65) Prior Publication Data
US 2011/0249797 A1    Oct. 13, 2011

(30) Foreign Application Priority Data
Nov. 12, 2008  (JP) ................................ 2008-289514

(51) Int. Cl.
*A61N 5/10* (2006.01)
(52) U.S. Cl.
USPC ......................................................... 378/65
(58) Field of Classification Search
USPC .......................................... 378/62, 64, 65, 69
See application file for complete search history.

(56) References Cited

U.S. PATENT DOCUMENTS

| 5,394,452 A | * | 2/1995 | Swerdloff et al. ............... 378/65 |
| 7,257,436 B2 | * | 8/2007 | Sasaki et al. ................... 600/428 |
| 2005/0054916 A1 | * | 3/2005 | Mostafavi ....................... 600/427 |

FOREIGN PATENT DOCUMENTS

| JP | 2001-161839 A1 | 6/2001 |
| JP | 2007-503926 A1 | 3/2007 |

OTHER PUBLICATIONS

International Search Report for International Application No. PCT/JP2009/69271 dated Dec. 10, 2009.

* cited by examiner

*Primary Examiner* — Irakli Kiknadze
(74) *Attorney, Agent, or Firm* — Kratz, Quintos & Hanson, LLP

(57) ABSTRACT

A radiation treatment system that can apply radiation to a respiratory moving organ (such as, a lung, a liver or the like) with high precision is provided. A radiation treatment system according to the present invention as solving means is characterized in that when medical treatment target position information obtained by executing pattern matching processing on the inside of each frame of a fluoroscopic X-ray image for detecting a medical treatment target position achieved under medical treatment on the basis of a template image of an area containing a medical treatment target position of a patient, which is achieved in advance, is within a predetermined error range with respect to the medical treatment target position information based on the template image, and also a timing is an application timing of medical treatment radiation which is set on the basis of motion information of a body surface, a signal for applying medical treatment radiation is generated; and in the other cases, a signal for stopping the application is generated, whereby the application of the medical treatment radiation is controlled on the basis of these signals.

7 Claims, 1 Drawing Sheet

RADIATION TREATMENT SYSTEM

BACKGROUND OF THE INVENTION

1. Technical Field

The present invention relates to a radiation treatment system that can apply radiation to a respiratory moving organ (such as, a lung, a liver or the like) with high precision.

2. Background Art

With respect to radiation treatment of cancers, it is important to specify an application position of radiation with high precision from the viewpoint of effective medical treatment of cancers, efficient use of radiation, reduction in adverse effects of exposure to normal tissues, etc. However, a respiratory moving organ (such as, a lung, a liver or the like) moves in connection with respiration; and thus, it is not easy to specify the position of cancer in these internal organs. Therefore, it has been hitherto executed to embed a metal marker around a cancer tissue in the body of a patient to enhance the contrast of a fluoroscopic image, thereby specifying the application position of the radiation (see, for example, Patent Document 1). However, this method is invasive; and thus, becomes burdensome to a patient. Accordingly, there is a method for specifying the application position of radiation with high precision without embedding any metal marker into the body of the patient.

Patent Document 1: JP-A-2000-167072

SUMMARY OF THE INVENTION

The present invention has for its object to provide a radiation treatment system that can apply radiation to a respiratory moving organ (such as, a lung, a liver or the like) with high precision without adopting any invasive method to a patient in which a metal marker for facilitating image recognition is embedded into the body.

The present inventors have exerted their efforts in their studies directed to the foregoing point; and consequently have found that difficulty in specifying an application position of radiation which is caused by lack of the contrast of a fluoroscopic image due to the non-use of a metal marker can be overcome by complementing the difficulty with motion information of the body surface.

The invention is directed to a radiation treatment system, which has been implemented on the basis of the above knowledge in that when medical treatment target position information obtained by executing pattern matching processing on the inside of each frame of a fluoroscopic X-ray image for detecting a medical treatment target position achieved under medical treatment on the basis of a template image of an area containing a medical treatment target position of a patient, which is achieved in advance, is within a predetermined error range with respect to the medical treatment target position information based on the template image, and also a timing is an application timing of medical treatment radiation which is set on the basis of motion information of a body surface, a signal for applying medical treatment radiation is generated; and in the other cases, a signal for stopping the application is generated, whereby the application of the medical treatment radiation is controlled on the basis of these signals.

Furthermore, the radiation treatment system is further characterized in that in the radiation treatment system, the template image is a fluoroscopic X-ray image.

Still furthermore, the radiation treatment system is further characterized in that in the radiation treatment system, the template image is a digital reconstructed image calculated from a computer tomographic image.

Furthermore, the radiation treatment system is further characterized in that in the radiation treatment system, respiration phase information is adopted as the motion information of the body surface, and a predetermined respiration phase timing is set as the application timing of the medical treatment radiation.

Furthermore, the radiation treatment system is further characterized in that in the radiation treatment system, an expiration timing is set as the application timing of the medical treatment radiation.

Furthermore, the radiation treatment system is characterized in that in the radiation treatment system, a condition that reference position information obtained by executing pattern matching processing on the inside of each frame of a fluoroscopic X-ray image for detecting a reference position achieved under medical treatment on the basis of a template image of an area containing a reference position other than the medical treatment target position of the patient, which is achieved in advance, is within a predetermined error range with respect to the reference position information based on the template image is added as a requisite condition for generating the signal for applying the medical treatment radiation.

Also, the radiation treatment system is characterized in that in the radiation treatment system, when the timing is the application timing of the medical treatment radiation set on the basis of the motion information of the body surface, a signal for applying X-ray for achieving a fluoroscopic X-ray image is generated, and a signal for stopping the application is generated in the other cases, whereby the application of the X-ray for achieving the fluoroscopic X-ray image is controlled on the basis of these signals.

According to the present invention, there can be provided a radiation treatment system that can apply radiation to a respiratory moving organ (such as, a lung, a liver or the like) with high precision without adopting any invasive method to a patient in which a metal marker for facilitating image recognition is embedded into the body.

EXPLANATION OF SYMBOLS

Figure 1:
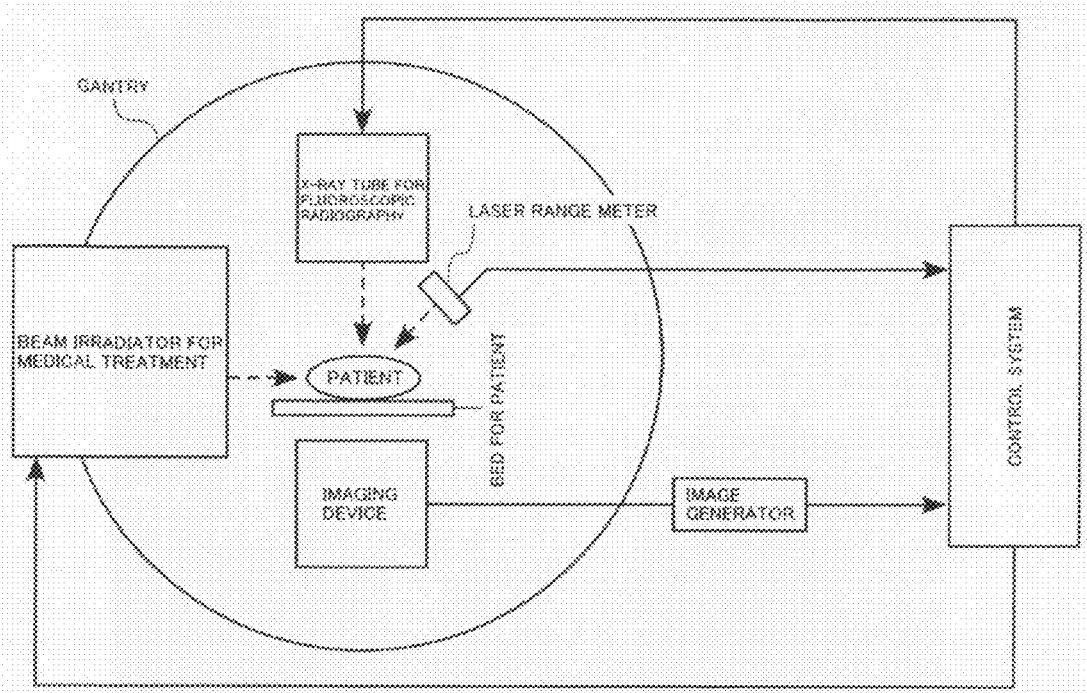
FIG. 1 is a conceptual diagram showing an example of a radiation treatment system according to the present invention.

A real-time fluoroscopic X-ray image of lung
B respiration phase signal
C medical treatment target position information detected by executing pattern matching processing
D generation pattern of gate signal to accelerator
1 medical treatment target position information based on template image
2 medical treatment target position information determined as being optimum by executing pattern matching processing
3 position information in craniocaudal direction
4 position information in right-and-left direction

DETAILED DESCRIPTION OF THE PREFERRED EMBODIMENTS

A radiation treatment system according to the present invention is characterized in that when medical treatment target position information obtained by executing pattern matching processing on the inside of each frame of a fluoroscopic X-ray image for detecting a medical treatment target position achieved under medical treatment on the basis of a template image of an area containing a medical treatment target position of a patient, which is achieved in advance, is within a predetermined error range with respect to the medical treatment target position information based on the template image, and also a timing is an application timing of medical treatment radiation which is set on the basis of motion information of a body surface, a signal for applying medical treatment radiation is generated; and in the other cases, a signal for stopping the application is generated, whereby the application of the medical treatment radiation is controlled on the basis of these signals.

Programming is executed so that application of medical treatment radiation (X-ray, positron or the like) is controlled by combining motion information of a body surface with medical treatment target position information of a cancer lesion or the like which is obtained by executing pattern matching processing under medical treatment; and a signal for applying medical treatment radiation is generated only when the medical treatment target position information obtained by executing the pattern matching processing under the medical treatment is within a predetermined error range with respect to the medical treatment target position information based on a template image and a timing is an application timing of the medical treatment radiation which is set on the basis of the motion information of the body surface. Accordingly, even when it is determined due to a lack of contrast of a fluoroscopic X-ray image caused by the non-use of a metal marker that the medical treatment target position information obtained by executing the pattern matching processing under the medical treatment is within the predetermined error range with respect to the medical treatment target position information based on the template image although it is actually out of the predetermined error range, the medical treatment radiation is not applied unless the timing is not the application timing of the medical treatment radiation which is settled on the basis of the motion information of the body surface, whereby the radiation can be applied to the medical treatment target position with high precision.

It is desirable to adopt respiration phase information as the motion information of the body surface. The respiration waveform is generally more stable under expiration than that under inspiration. Therefore, medical treatment radiation can be applied to a respiratory moving organ (such as, a lung, a liver or the like) with high precision by setting the expiration timing as an application timing of medical treatment radiation. However, the application timing of the medical treatment radiation is not limited to that under expiration. The method of obtaining the motion information of the body surface is not limited to a specific one. However, in order to control the application of the medical treatment radiation with high precision and high reliability, it is desirable to obtain it as extracorporeal information by utilizing a sensor mounted outside the body, such as, e.g., a laser range meter, a strain sensor or the like.

FIG. 1 is a conceptual diagram showing an example of a radiation treatment system (for example, positron medical treatment system) according to the present invention. This radiation treatment system comprises a medical treatment radiation applying device (may be an existing linac), an X-ray fluoroscope for detecting a medical treatment target position, a laser range meter for obtaining respiration phase information and a control system as a basic construction. When medical treatment is conducted, a fluoroscopic X-ray image of a patient on a patient bed inside a gantry is achieved on a real-time basis, and also respiration phase information is obtained by the laser range meter. In the control system, the achieved fluoroscopic X-ray image is subjected to the pattern matching processing in each frame on the basis of a template image (may be a fluoroscopic X-ray image achieved when a medical treatment plan is drawn up or a digital reconstructed (DRR) image calculated from a computer tomographic (CT) image) of an area containing a medical treatment target position of a patient which is achieved in advance, whereby it is determined whether the medical treatment target position information is within a predetermined error range (for example, within a range of ±2 mm) with respect to the medical treatment target position information based on the template image. When the medical treatment target position information is determined as being within the error range, it is set as a requisite condition for generating a signal for applying medical treatment radiation (a gate signal to an accelerator, the same shall apply hereinafter). On the other hand, for example, a timing of applying medical treatment radiation is set to an expiration timing identified from respiration phase information, and the expiration timing is set as a requisite condition for generating a signal for applying medical treatment radiation. When both the requisite conditions are satisfied, the signal for applying the medical treatment radiation is generated, whereby the medical treatment radiation is applied to a patient. By controlling the application of the medical treatment radiation as described above, radiation can be applied to a respiratory moving organ (such as, a lung, a liver or the like) with high precision; and thus, the total amount of radiation exposure of the medical treatment radiation to the patient can be reduced. It is necessarily desirable that the body position of the patient under medical treatment is as coincident as possible with the body position when a template image was achieved. Accordingly, when medical treatment is started, on the basis of comparison of physical appearance of a patient based on a television monitor or an image, it is desired to arbitrarily adjust the position of a bed so that the body position of the patient at that time is made coincident with that when the template image was achieved. Furthermore, a mask, a mat, a restraining belt or the like may be used to fix the patient.

Figure 2:
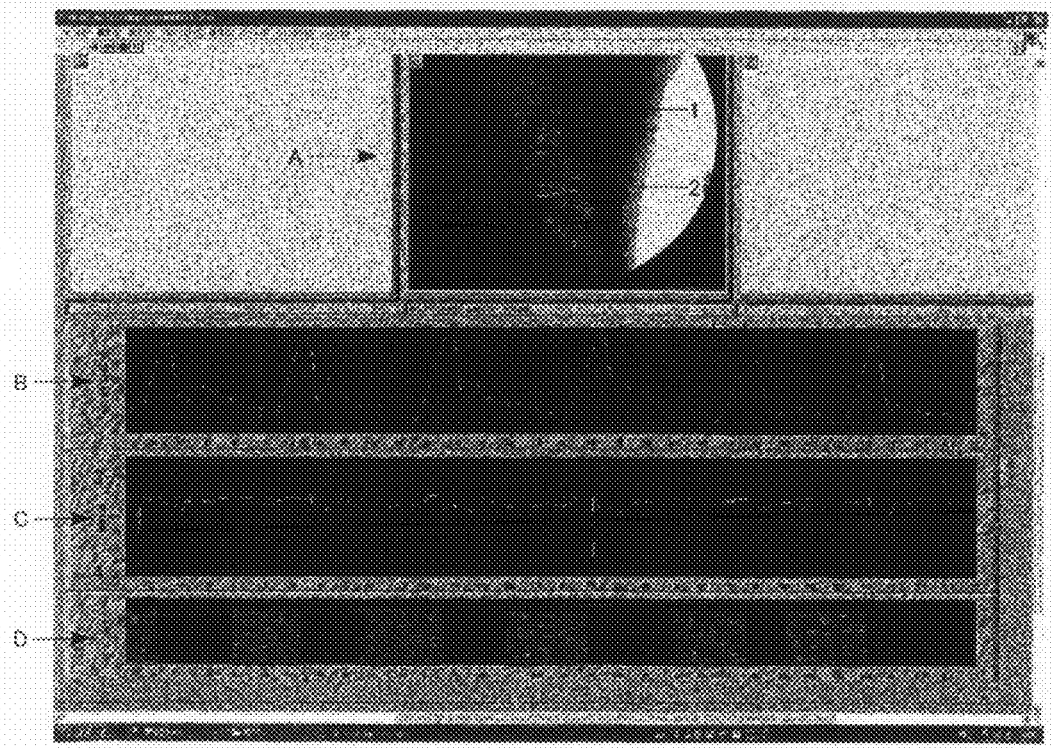
FIG. 2 is a display example on a computer screen which is subjected to data processing on a real-time basis under medical treatment.

FIG. 2 shows a display example on a computer screen which is subjected to data processing on a real-time basis under medical treatment. Reference character A represents a real-time fluoroscopic X-ray image of a lung; reference numeral 1 represents medical treatment target position information based on a template image of an area containing a medical treatment target position of a patient which is achieved in advance; and reference numeral 2 represents medical treatment target position information determined as being optimum by executing, on a real-time basis, pattern matching processing on the inside of each frame of a real-time fluoroscopic X-ray image on the basis of the template image. Reference character B represents a respiration phase signal; and reference character C represents medical treatment target position information detected by executing the real-time pattern matching processing (reference numeral 3 represents a craniocaudal direction, and reference numeral 4 represents a right-and-left direction). Reference character D represents a generation pattern of a gate signal to an accelerator for applying medical treatment radiation to a patient, and programming is executed so that when the real-time medical treatment target position information represented by reference numeral C is within a predetermined error range with respect to the medical treatment target position information based on the template image both in the craniocaudal direction and the right-and-left direction, and a timing is an expiration timing identified on the basis of the reference numeral B, a signal is generated and no signal is generated at the other timings.

In order to implement radiation application to a medical treatment target position with higher precision, a condition that reference position information obtained by executing pattern matching processing on the inside of each frame of a fluoroscopic X-ray image for detecting a reference position achieved under medical treatment on the basis of a template image of an area containing a reference position other than the medical treatment target position of the patient, which is achieved in advance, is within a predetermined error range with respect to the reference position information based on the template image may be added as a requisite condition for generating the signal for applying the medical treatment radiation. A diaphragmatic site or a bone structure of any site may be used as an available reference position as described above.

In the present invention, the achievement of the fluoroscopic X-ray image for detecting the medical treatment target position may be set to be unnecessary when the timing is not the application timing of the medical treatment radiation which is set on the basis of the motion information of the body surface. Accordingly, when the timing is the application timing of the medical treatment radiation set on the basis of the motion information of the body surface, a signal for applying X-ray for achieving a fluoroscopic X-ray image may be generated, and a signal for stopping the application may be generated in the other cases, whereby the application of the X-ray for achieving the fluoroscopic X-ray image is controlled on the basis of these signals. The control as described above may be performed by signal transmission from the control system to an X-ray tube for fluoroscopic radiography as shown in FIG. 1. The fluoroscopic X-ray image is achieved while the timing is limited to the timing of applying the medical treatment radiation set on the basis of the motion information of the body surface, whereby the total amount of radiation exposure of the X-ray for achieving the fluoroscopic X-ray image to the patient can be reduced.

Furthermore, the radiation treatment system according to the present invention does not exclude use of a metal marker, and when a metal marker is used, radiation can be applied to a medical treatment target position with higher precision.

The present invention has an industrial applicability in view of providing a radiation treatment system that can apply radiation to a respiratory moving organ (such as, a lung, a liver or the like) with high precision.

The invention claimed is:

1. A radiation treatment system, comprising:
a first signal generator for generating a first signal for applying medical treatment radiation when medical treatment target position information obtained by executing pattern matching processing on the inside of each frame of a fluoroscopic X-ray image for detecting a medical treatment target position achieved under medical treatment on the basis of a template image of an area containing a medical treatment target position of a patient, which is achieved in advance, is within a predetermined error range with respect to the medical treatment target position information based on the template image, and also a timing is an application timing of medical treatment radiation which is set on the basis of motion information of a body surface as extracorporeal information; and
in the other cases, a second signal generator for generating a second signal for stopping the medical treatment radiation application, whereby the application of the medical treatment radiation is controlled on the basis of the first and second signals.

2. The radiation treatment system according to claim 1, wherein the template image is a fluoroscopic X-ray image.

3. The radiation treatment system according to claim 1, wherein the template image is a digital reconstructed image calculated from a computer tomographic image.

4. The radiation treatment system according to claim 1, wherein respiration phase information is adopted as the motion information of the body surface, and a predetermined respiration phase timing is set as the application timing of the medical treatment radiation.

5. The radiation treatment system according to claim 4, wherein an expiration timing is set as the application timing of the medical treatment radiation.

6. The radiation treatment system according to claim 1, wherein a condition that reference position information obtained by executing pattern matching processing on the inside of each frame of a fluoroscopic X-ray image for detecting a reference position achieved under medical treatment on the basis of a template image of an area containing a reference position other than the medical treatment target position of the patient, which is achieved in advance, is within a predetermined error range with respect to the reference position information based on the template image is added as a requisite condition for generating the signal for applying the medical treatment radiation.

7. The radiation treatment system according to claim 1, wherein when the timing is the application timing of the medical treatment radiation set on the basis of the motion information of the body surface, a first signal for applying X-ray for achieving a fluoroscopic X-ray image is generated, and a second signal for stopping the application is generated in the other cases, whereby the application of the X-ray for achieving the fluoroscopic X-ray image is controlled on the basis of the first and second signals.

* * * * *